United States Patent
Hogan et al.

(10) Patent No.: US 7,516,765 B2
(45) Date of Patent: Apr. 14, 2009

(54) AIR VENT FOIL CUTTER

(75) Inventors: Brendan Hogan, Gort (IE); Rolf Rainer Scheu, Frankfurt am Main (DE)

(73) Assignee: Filtertek Inc., Hebron, IL (US)

(*) Notice: Subject to any disclaimer, the term of this patent is extended or adjusted under 35 U.S.C. 154(b) by 528 days.

(21) Appl. No.: 11/284,636

(22) Filed: Nov. 21, 2005

(65) Prior Publication Data

US 2006/0137763 A1 Jun. 29, 2006

(30) Foreign Application Priority Data

Nov. 22, 2004 (DE) .................. 20 2004 018 089 U
Jun. 30, 2005 (DE) .................. 20 2005 010 459 U

(51) Int. Cl.
*B65B 1/04* (2006.01)
(52) U.S. Cl. .................. 141/329; 141/288; 222/89; 222/189.09; 604/403; 604/405; 604/520
(58) Field of Classification Search .................. 141/1, 141/286, 320, 325, 329, 330; 604/520, 19, 604/405, 403, 411, 415; 215/278; 222/89, 222/91, 83, 189.09, 479
See application file for complete search history.

(56) References Cited

U.S. PATENT DOCUMENTS

| | | | |
|---|---|---|---|
| 2,630,874 A | 3/1953 | Langdon |
| 2,758,609 A | 8/1956 | Dickert et al. |
| 2,980,032 A | 4/1961 | Schneider |
| 3,084,707 A | 4/1963 | Frye |
| 3,238,056 A | 3/1966 | Pall |
| 3,270,771 A | 9/1966 | Morgan et al. |
| 3,599,657 A | 8/1971 | Maldays |
| 3,633,605 A | 1/1972 | Smith |
| 3,658,183 A | 4/1972 | Best et al. |
| 3,779,274 A | 12/1973 | Kelly |
| 3,782,083 A | 1/1974 | Rosenberg |
| 3,932,153 A | 1/1976 | Byrns |

(Continued)

FOREIGN PATENT DOCUMENTS

BE   1 009 834 A6   10/1997

(Continued)

OTHER PUBLICATIONS

Christians, Rolf, "Membranen inder Pneumatik," *Fluid*, pp. 39-46 (Apr. 1980).

*Primary Examiner*—Gregory L Huson
*Assistant Examiner*—Jason K Niesz
(74) *Attorney, Agent, or Firm*—Brinks Hofer Gilson & Lione

(57) ABSTRACT

Apparatus (1) for the introduction of air into enteral containers (2). A valve (14) is provided in a connection member (4) connecting the enteral set with the container (2) containing the enteral liquid and controls the introduction of air corresponding to the consumption of the enteral liquid. The valve (14) may include an oleophobic filter material that covers the air inlet (16) projecting into the connection member (4). The valve (14) on the side facing the container (2) is provided with a cutting device (20) for the foil closure of aluminum or plastics closing the container (2) in its initial delivered state. The cutting device (20) may be a circular or partly circular projection (28) rising from a low side (30) to a high side (32).

49 Claims, 7 Drawing Sheets

U.S. PATENT DOCUMENTS

| | | | |
|---|---|---|---|
| 3,966,520 A | 6/1976 | Fallenbeck et al. | |
| 4,022,258 A | 5/1977 | Steidley | |
| 4,046,276 A * | 9/1977 | Winchell et al. | 215/250 |
| 4,089,349 A | 5/1978 | Schenk | |
| 4,141,379 A | 2/1979 | Manske | |
| 4,148,732 A | 4/1979 | Burrow et al. | |
| 4,181,477 A | 1/1980 | Litt | |
| 4,188,978 A | 2/1980 | De Lorenzo | |
| 4,237,880 A | 12/1980 | Genese | |
| 4,241,756 A | 12/1980 | Bennett et al. | |
| 4,343,305 A | 8/1982 | Bron | |
| 4,355,639 A | 10/1982 | Di Salvo | |
| 4,404,006 A | 9/1983 | Williams et al. | |
| 4,415,003 A | 11/1983 | Paradis et al. | |
| 4,459,139 A | 7/1984 | vonReis et al. | |
| 4,534,764 A | 8/1985 | Mittleman et al. | |
| 4,556,086 A | 12/1985 | Raines | |
| 4,593,720 A | 6/1986 | Bergandy | |
| 4,646,781 A | 3/1987 | McIntyre | |
| 4,664,800 A | 5/1987 | Raines et al. | |
| 4,670,510 A | 6/1987 | Kobayashi et al. | |
| 4,712,583 A | 12/1987 | Pelmulder et al. | |
| 4,749,003 A | 6/1988 | Leason | |
| 4,754,889 A * | 7/1988 | Debetencourt | 215/232 |
| 4,768,547 A | 9/1988 | Danby et al. | |
| 4,793,503 A | 12/1988 | Towns et al. | |
| 4,846,215 A | 7/1989 | Barree | |
| 4,857,068 A * | 8/1989 | Kahn | 604/405 |
| 4,874,513 A | 10/1989 | Chakraborty et al. | |
| 4,958,661 A | 9/1990 | Holtermann et al. | |
| 4,966,199 A | 10/1990 | Ruschke | |
| 4,986,904 A | 1/1991 | Bugar et al. | |
| 4,997,429 A * | 3/1991 | Dickerhoff et al. | 604/411 |
| 5,011,555 A | 4/1991 | Sager | |
| 5,025,829 A | 6/1991 | Edwards et al. | |
| 5,041,105 A * | 8/1991 | D'Alo et al. | 604/411 |
| 5,125,522 A | 6/1992 | Pezzoli et al. | |
| 5,147,545 A | 9/1992 | Despard et al. | |
| 5,215,538 A | 6/1993 | Larkin | |
| 5,230,727 A | 7/1993 | Pound et al. | |
| 5,265,770 A | 11/1993 | Matkovich et al. | |
| 5,269,917 A | 12/1993 | Stankowski | |
| 5,443,723 A | 8/1995 | Stankowski et al. | |
| 5,453,097 A | 9/1995 | Paradis | |
| 5,500,003 A | 3/1996 | Guala et al. | |
| 5,505,326 A * | 4/1996 | Junko | 220/278 |
| 5,520,661 A | 5/1996 | Lal et al. | |
| 5,603,792 A | 2/1997 | Guala et al. | |
| 5,617,897 A | 4/1997 | Myers | |
| 5,749,861 A | 5/1998 | Guala et al. | |
| 5,771,935 A | 6/1998 | Myers | |
| 5,782,383 A | 7/1998 | Robinson | |
| 5,935,100 A | 8/1999 | Myers | |
| 6,086,762 A | 7/2000 | Guala | |
| 6,168,653 B1 | 1/2001 | Myers | |
| 6,290,682 B1 | 9/2001 | Myers | |
| 6,579,342 B2 | 6/2003 | Wang | |
| 6,708,714 B1 | 3/2004 | Mijers | |
| 6,779,669 B2 * | 8/2004 | Schann | 210/446 |
| 2002/0144595 A1 * | 10/2002 | Wang et al. | 95/46 |
| 2002/0144959 A1 * | 10/2002 | Wang et al. | 95/46 |
| 2004/0074925 A1 | 4/2004 | Michel | |
| 2004/0153047 A1 * | 8/2004 | Blank et al. | 604/408 |
| 2004/0211484 A1 * | 10/2004 | Fournie et al. | 141/329 |
| 2006/0259004 A1 * | 11/2006 | Connell et al. | 604/403 |
| 2007/0112323 A1 * | 5/2007 | Daly | 604/411 |

FOREIGN PATENT DOCUMENTS

| | | |
|---|---|---|
| DE | 667 675 | 4/1934 |
| DE | 1 695 553 | 3/1953 |
| DE | 1 675 370 | 2/1954 |
| DE | 2 502 673 A1 | 7/1976 |
| DE | 25 13 350 A1 | 10/1976 |
| DE | 27 13 618 C2 | 10/1977 |
| DE | 29 19 343 A1 | 11/1980 |
| DE | 30 35 301 A1 | 4/1981 |
| DE | 29 49 262 A1 | 6/1981 |
| DE | 32 15 329 A1 | 12/1982 |
| DE | 86 03 917 U1 | 5/1986 |
| DE | 36 32 412 A1 | 3/1988 |
| DE | 38 03 380 | 8/1989 |
| DE | 40 39 814 A1 | 6/1992 |
| DE | 92 09 491.0 | 10/1992 |
| DE | 41 42 494 A1 | 7/1993 |
| DE | 42 01 258 A1 | 7/1993 |
| DE | 93 19 810.8 U1 | 3/1994 |
| DE | 43 09 262 A1 | 6/1994 |
| DE | 43 04 949 A1 | 8/1994 |
| DE | 93 10 673.4 | 9/1994 |
| DE | 43 15 701 A1 | 11/1994 |
| DE | 29 501 239 | 4/1995 |
| DE | 691 09 240 T2 | 10/1995 |
| DE | 196 05 217 | 2/1996 |
| DE | 296 10 419.1 | 12/1996 |
| DE | 195 45 421 A1 | 6/1997 |
| DE | 196 43 360 C1 | 5/1998 |
| DE | 197 49 562 C1 | 4/1999 |
| DE | 102 19 994 A1 | 12/2003 |
| DE | 20 2004 009 831 U1 | 8/2004 |
| DE | 20 2004 009 521 U1 | 10/2004 |
| EP | 0 072 800 B1 | 3/1983 |
| EP | 0 379 047 A | 7/1990 |
| EP | 0 459 498 A1 | 12/1991 |
| EP | 0 562 246 A1 | 9/1993 |
| EP | 0 612 537 A2 | 8/1994 |
| EP | 0 612 537 A3 | 8/1994 |
| EP | 0 652 018 B1 | 10/1996 |
| EP | 0 812 596 A1 | 12/1997 |
| EP | 0 878 628 A2 | 11/1998 |
| EP | 0 887 085 A2 | 12/1998 |
| EP | 0 934 757 A2 | 8/1999 |
| EP | 1 063 956 B1 | 1/2001 |
| EP | 1 088 765 A | 4/2001 |
| FR | 2 666 745 A | 3/1992 |
| GB | 439 278 A | 12/1935 |
| GB | 811 818 | 4/1959 |
| GB | 2 027 168 A | 2/1980 |
| WO | WO 88/02639 | 4/1988 |
| WO | WO 89/02764 | 4/1989 |
| WO | WO 91/11641 | 8/1991 |
| WO | WO 93/10015 A | 5/1993 |
| WO | WO 96/03166 | 2/1996 |
| WO | WO 97/03712 | 2/1997 |
| WO | WO 97/47339 | 12/1997 |

* cited by examiner

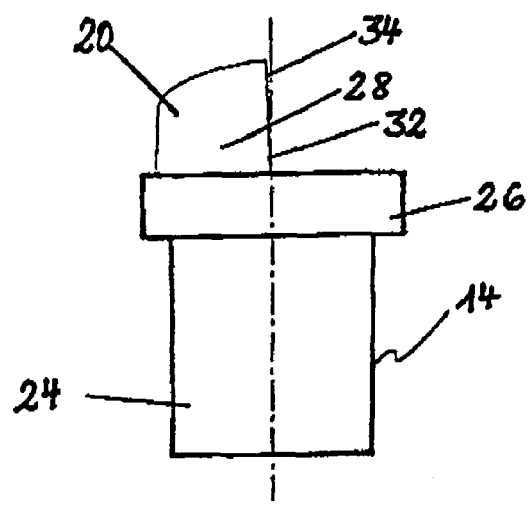
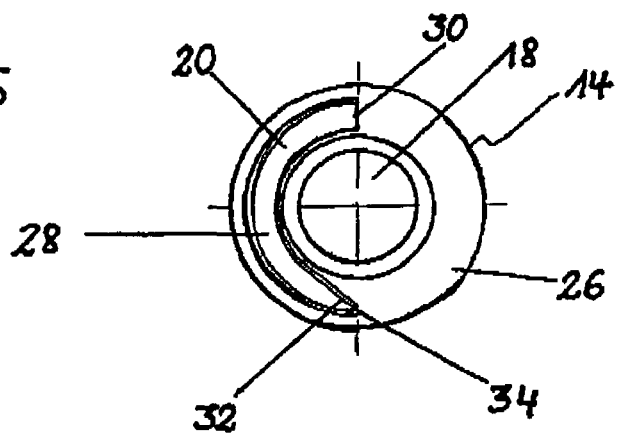
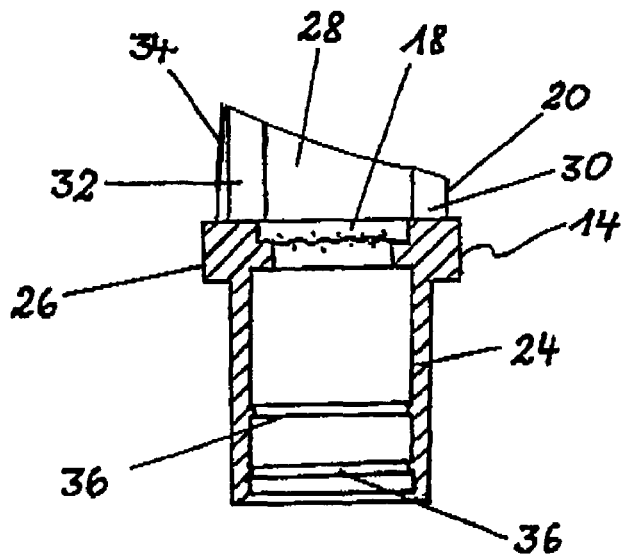

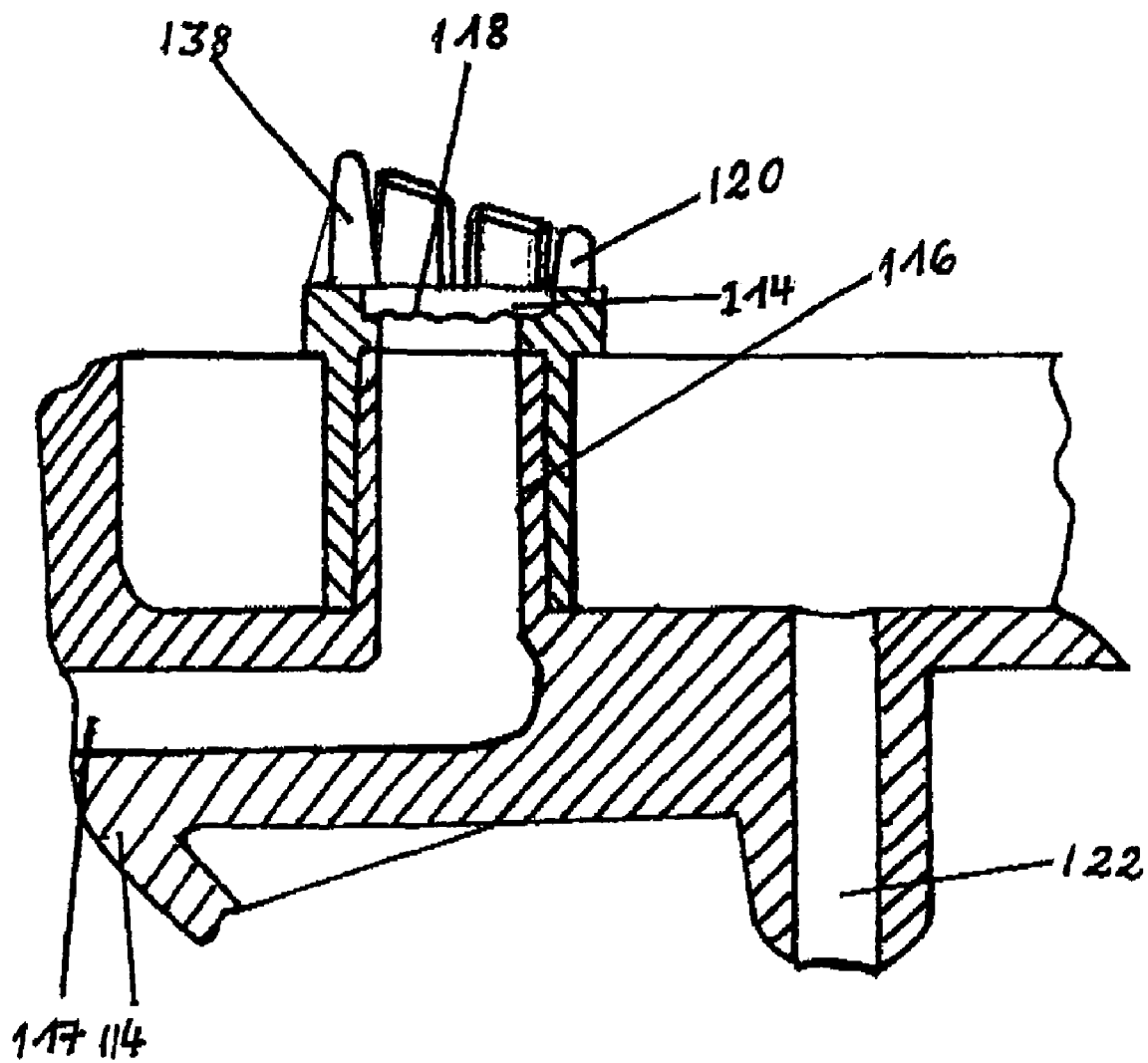

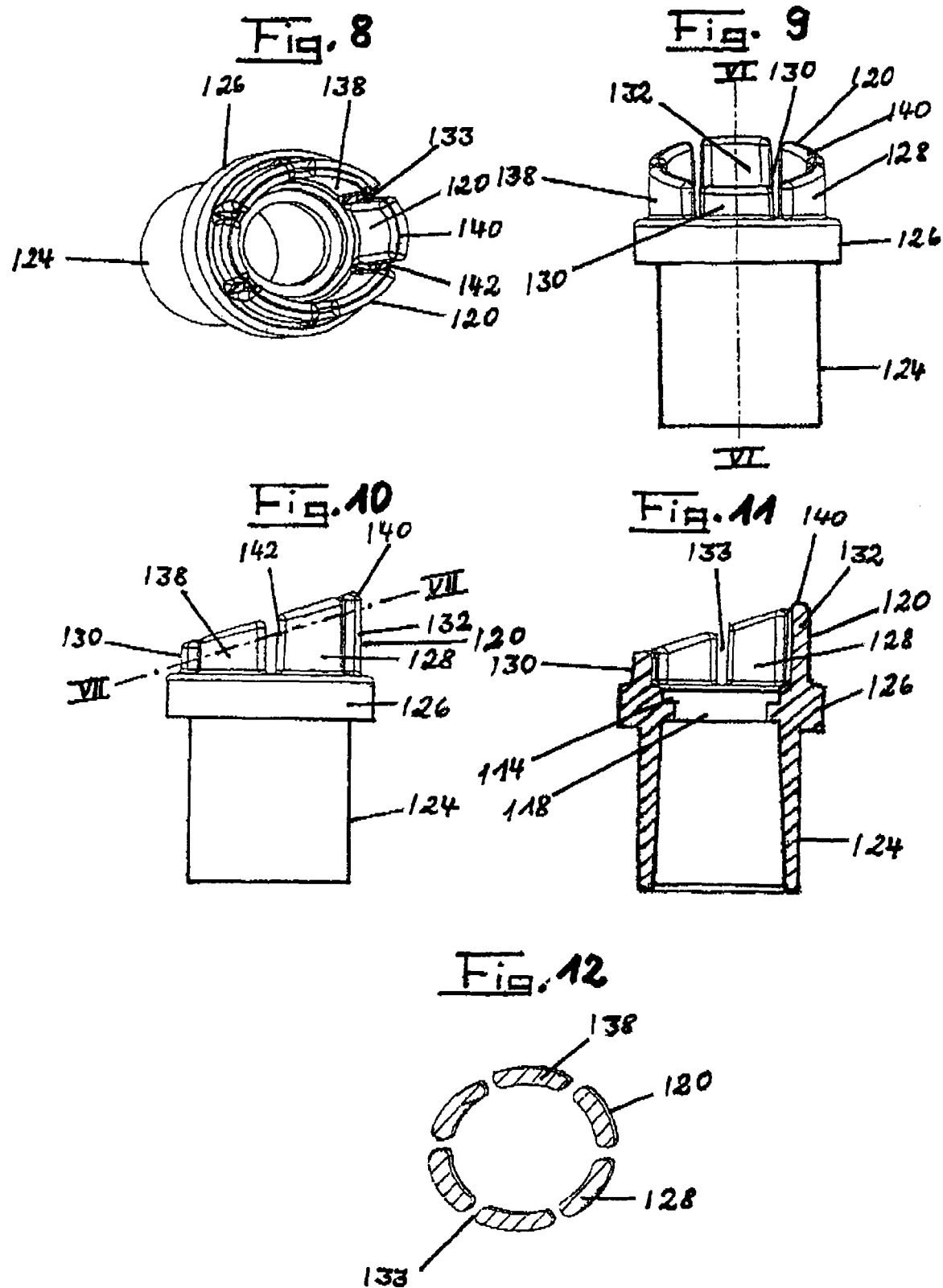

AIR VENT FOIL CUTTER

Applicant claims, under 35 U.S.C. § 119, the benefit of priority of the filing date of Nov. 22, 2004 of German utility model application DE 20 2004 018 089.8 and of the filing date of Jun. 30, 2005 of German utility model application DE 20 2005 010 459.0.

FIELD OF THE INVENTION

The invention relates to an apparatus for the introduction of air into enteral containers having a valve which is positioned in a connection member connecting the enteral instrument with the container containing the enteral liquid and which controls the introduction of air corresponding to the consumption of the enteral liquid.

BACKGROUND OF THE INVENTION

Because air valves control the introduction of air into a gravity feed enteral liquid system, the rate of introduction of the enteral liquid into the patient is ensured and the consumption of the enteral liquid in the gravity feed proceeds without difficulties. Up to now, the connection members for the enteral liquid containers usually were formed by screw caps screwable onto container check valves. However, this assembly does not work satisfactorily in all cases. Additionally, enteral liquids are usually delivered in containers which, in addition to the screw cap forming the closure, are closed by a welded aluminum or plastic planar foil piece. Therefore, such a closure foil or plastic must, in a separate step, be opened before the enteral liquid container can be used by screwing or pressing the container onto the connection members associated with the enteral liquid delivery assembly system.

It is therefore the task to be solved by the present invention to design an apparatus of the above-identified kind in such a way that, on the one hand, the valve is safe and effective and simultaneously the additional step of the cumbersome opening of the closure foil or plastic of the enteral liquid container is avoided.

BRIEF SUMMARY OF THE INVENTION

This task is solved in an apparatus of the above-identified kind by the features that the valve comprises an oleophobic filter material covering the air inlet projecting into the connection member and that the valve on the side facing the container is provided with a cutting device for the foil of aluminum or plastics closing the container in its delivered state. The cutting device may comprise a circular or partly circular projection rising from a low side to a high side.

The oleophobic filter material can function as a check valve since the material rejects oily substances and lets air pass without difficulty. Enteral liquids are basically solutions containing lipides, fats, emulsions, multi-vitamins, and oils. During the artificial feeding of a patient, the oleophobic filter material is in contact with the solution and makes it possible that air can get into the container corresponding to the consumption of the solution such that the flow to the patient is maintained. The additional cutting device on the valve projecting in the direction of the container automatically opens the closure foil during the connection with the container such that a simple screwing on or pressing on of the connection member renders the enteral instrument operative without additional manipulation.

It is possible in singular cases that during the pressing of the apparatus into the foil container closure at time of delivery, it is not pressed deep enough, and then under unfavorable conditions a kind of a flap from the foil material can be formed which is not completely separated from the foil material. Such flap possibly can close the cutting device again and thereafter close the air inlet again like a flap valve. Accordingly, a preferred embodiment includes a circular or partly circular projection separated into a number of segments by windows or incisions, and also these segments may reach down to a head section. These windows or incisions in the projecting cutting device may provide for keeping the air inlet open. In this connection, the shape of the windows or incisions may vary to accomplish the desired function of keeping the air inlet open. This embodiment may provide for a complete emptying of the container due to the fact that the small volume usually remaining in the bottle neck is emptied, too, due to the multiple piercings through the closure foil.

An aspect of an embodiment is that the filter material is mounted in a shell-shaped housing which can be put over the air inlet. This has the advantage that the connection members used until now do not have to be altered since these already are having a tube-shaped connection boss onto which until now the usual check valve was mounted.

Another aspect of an emobodiment is that the housing comprises plastic and the filter material is connected therewith by overmoulding. This enables a cost effective mass production.

Yet another aspect is that the filter material is positioned in the enlarged head section of the housing.

A further aspect is that the cutting device is formed unitary with the head section by overmoulding. In this connection a preferred embodiment has a rise of the circular projection from the low side to the high side of about 20°, with reference to the plane of the container foil seal or the coplanar base of the cutting device.

Another aspect of an embodiment is that the circular projection is divided into segments, such as six in number, by incisions or windows reaching down to the head section. Yet another aspect in detail in this connection is that a cutting edge is provided on the circular projection or the segments, respectively, at the upper edge thereof. This embodiment provides an easy cutting of the foil closing the container.

Further, an aspect is that the edges of the incisions opposite to each other are provided with cutting edges, too. This embodiment also provides an easy cutting of the foil closing the container. Yet another aspect in detail is that the incisions narrow in the direction approaching the head section, wherein a taper of 2° is especially preferred. This additionally facilitates removal of the apparatus from the plastic injection mold face after the injection molding is completed.

Still another aspect is that the wall thickness of the projection decreases from the low end to the high end thereof, and from the bottom to top, such that at the high end a cutting edge is formed.

Further an aspect is that the interior of the housing is slightly conical to provide for a clamping fit with the air inlet of the connector. Alternatively it is possible to provide the interior of the housing with annular unitary projections to provide for a positive or friction fit with the air inlet.

Other features and advantages of the present invention will become more fully apparent from the following description of the preferred embodiments, the appended claims, and the accompanying drawings.

BRIEF DESCRIPTION OF SEVERAL VIEWS OF THE DRAWINGS

FIG. 4 is an enlarged side view of the apparatus according to FIG. 3;

FIG. 5 is a top view of the apparatus according to FIG. 4;

FIG. 6 is a cross-sectional view of the apparatus according to FIGS. 4 and 5;

FIG. 7 is an enlarged cross-sectional view of FIG. 1 in the area of the air inlet with a second embodiment;

FIG. 8 is a perspective view of the apparatus according to FIG. 7 in an angle from above;

FIG. 9 is a side view of the apparatus according to FIG. 8 seen from the low side of the projection;

FIG. 10 is a side view of the apparatus according to FIG. 9;

FIG. 11 is a cross-sectional view along the line VI-VI of FIG. 9;

FIG. 12 is a cross-sectional view along the line VII-VII of FIG. 10, and

DETAILED DESCRIPTION OF THE INVENTION

Figure 1:
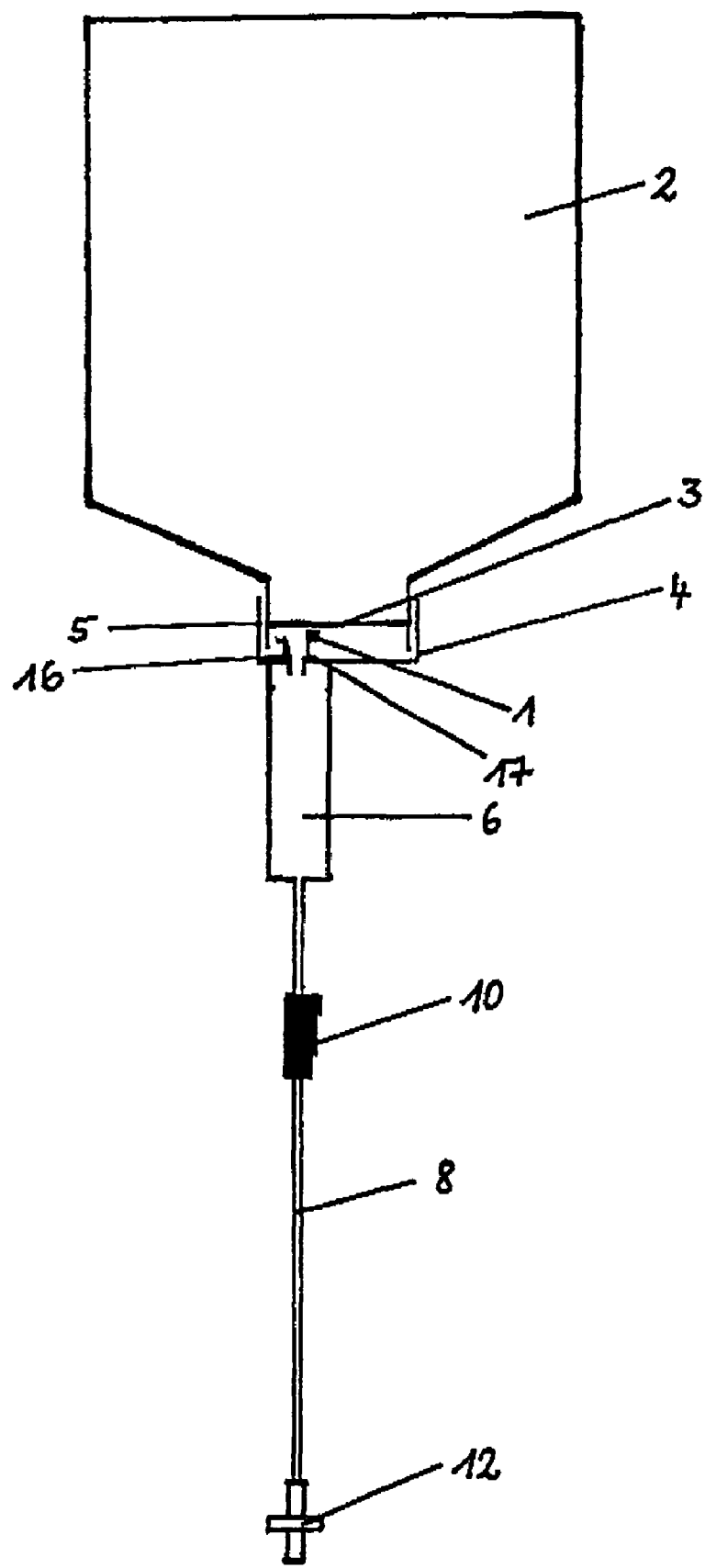
FIG. 1 is a schematic view of the complete gravity feed enteral set containing the apparatus embodiment.

In the schematic view according to FIG. 1 the apparatus 1 according to the invention is included in an enteral set. The enteral set is connected by means of a connection member 4 to a container 2 containing the enteral liquid and which in the state shown additionally is closed by a foil closure 3. In the embodiment shown the connection member 4 is a screw cap 5 which is not completely screwed onto the container 2 such that the foil closure is still undamaged. The screw cap 5 further includes a drip chamber 6 which by a connection line 8 controlled by a roller clamp 10 is connected to a probe 12 to be inserted into the patient. The enteral liquid contained in the container 2 is fed into the patient by gravity feed via the drip chamber 6 and controlled by the roller clamp 10.

To start and to maintain the gravity feed of the enteral liquid from the container 2 the connection member 4 includes a valve 14 which is positioned in an air inlet 16 and which controls the introduction of air into the container 2 corresponding to the consumption of the enteral liquid.

From FIGS. 2 to 6 details of the apparatus 1 are shown in more detail. As shown, the valve 14 is not a check valve but rather is an oleophobic filter material 18. Oleophobic filter material 18 repels oily and fatty substances, which are in the enteral liquid in container 2. The oleophobic filter material 18 covers the air inlet 16 projecting into the connection member 4 such that air can flow into the container 2, while the oily enteral liquid is rejected by the oleophobic filter material 18.

Additionally the valve 14 is provided with a cutting device generally designated 20 facing into container 2 which during the connection of the connection member 4 with the container 2 cuts the foil closing the container 2 when it is in the delivered state.

Figure 2:
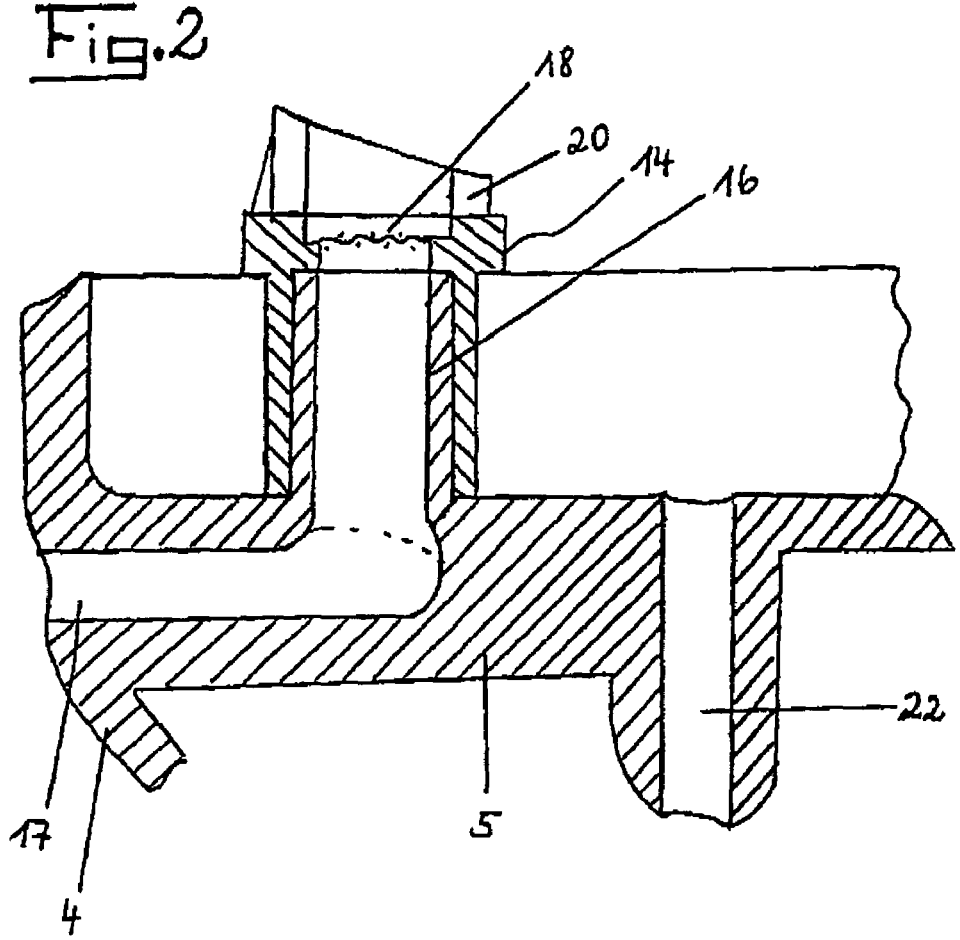
FIG. 2 is an enlarged cross-sectional view of a portion of FIG. 1 in the area of the air inlet according to a first embodiment.
Figure 3:
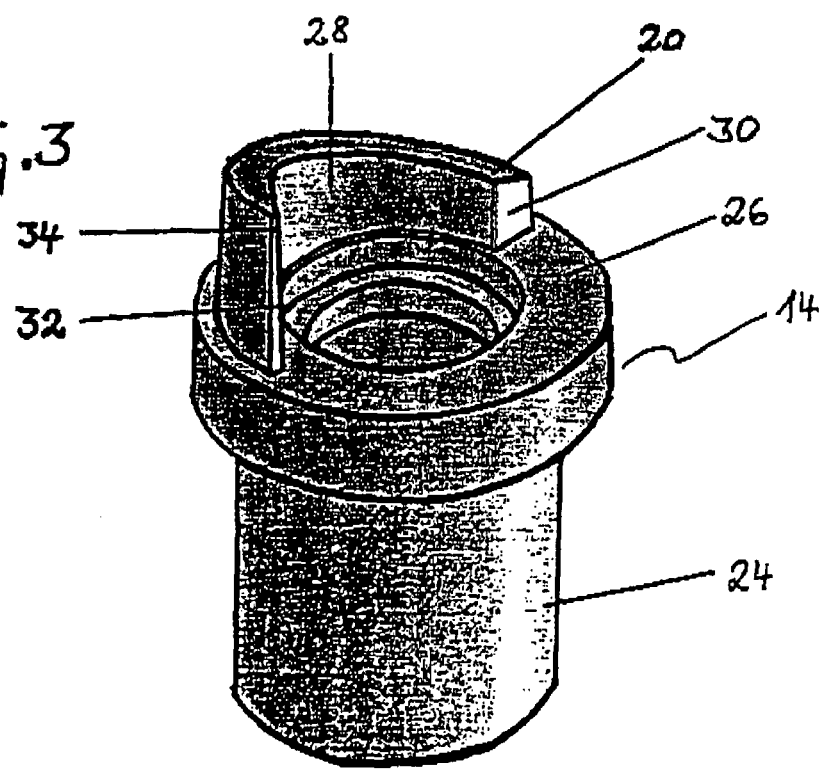
FIG. 3 is a perspective view of the first embodiment of the apparatus.
Figure 13:
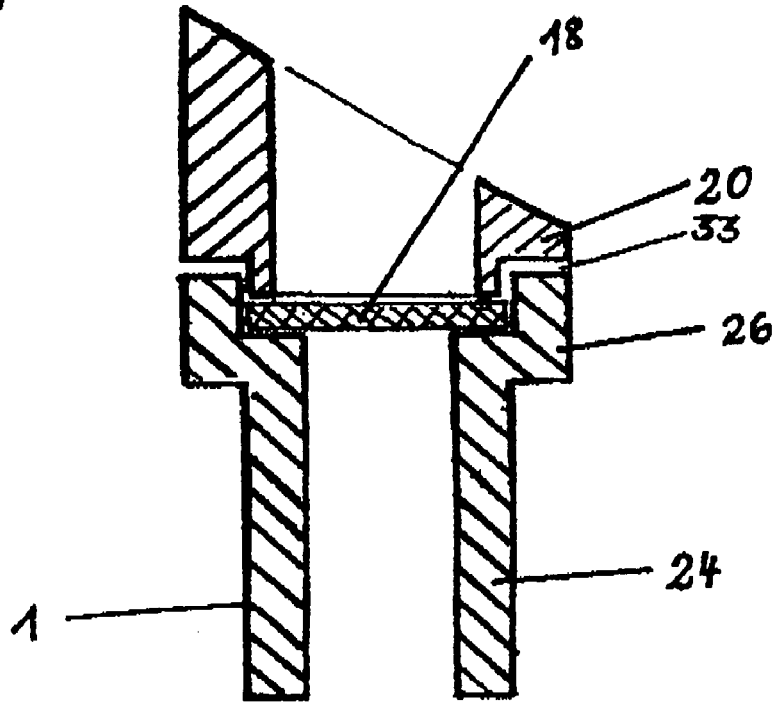
FIGS. 13 to 16 are cross-sectional views of alternative embodiments to show the technique of overmolding.
Figure 14:
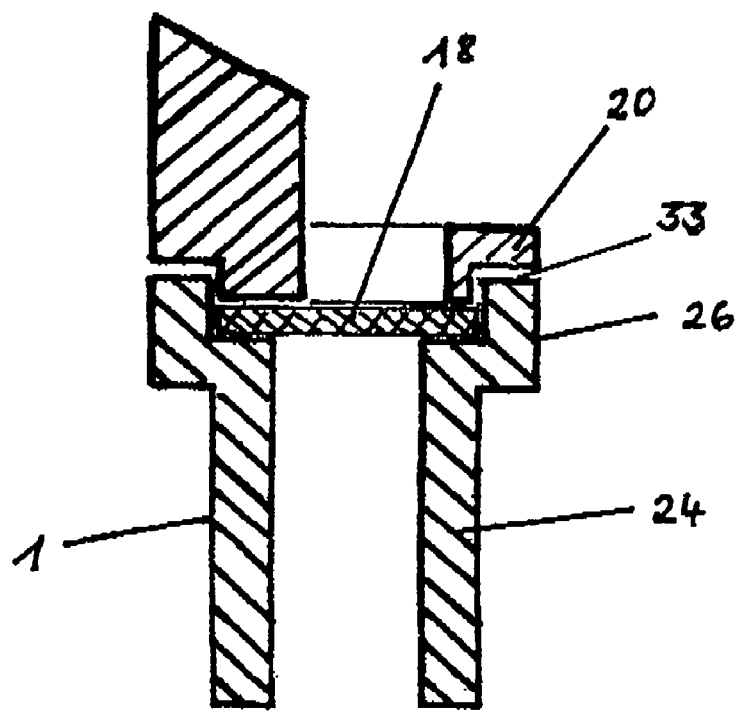
Figure 15:
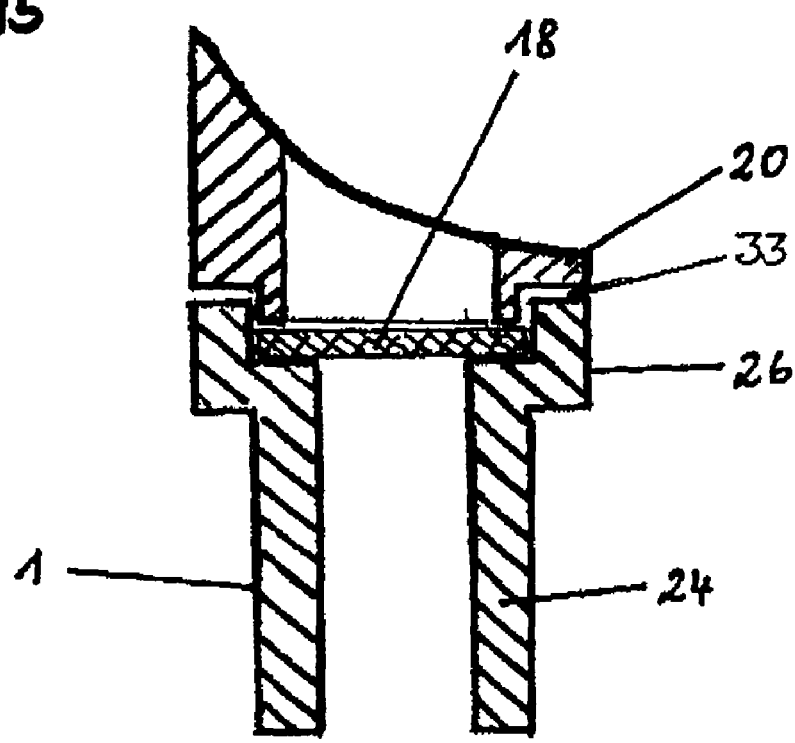
Figure 16:
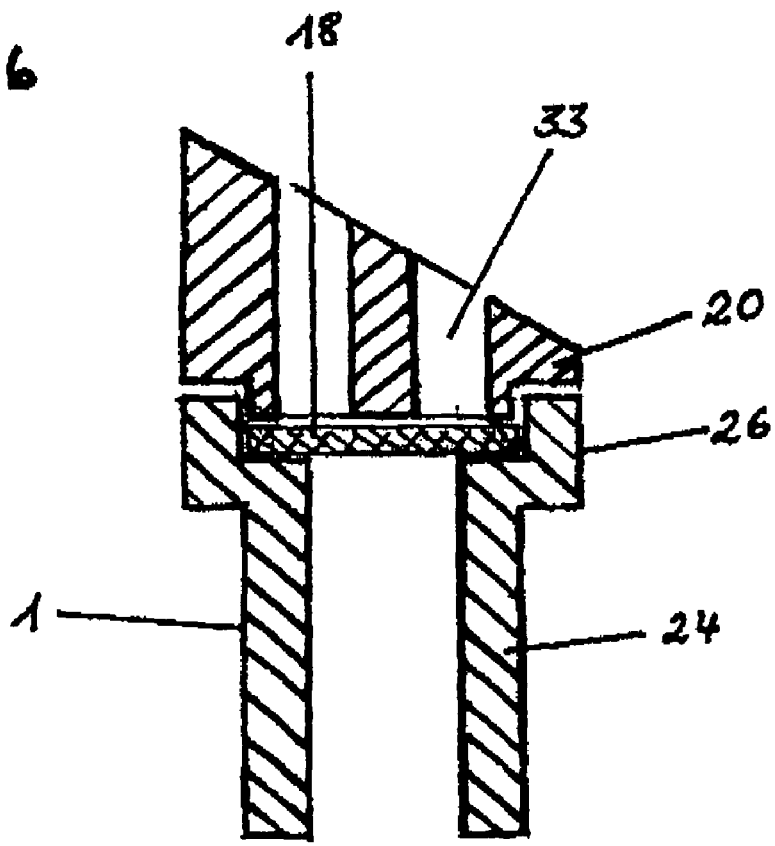

As can be noted from FIG. 2, while further details are shown in FIGS. 3 to 6, the filter material 18 is positioned in a shell-shaped housing 24 which can be put over the air inlet 16. The housing 24 preferably comprises plastic and has filter material 18 positioned therein, and may be secured by overmolding. The housing 24 may have an enlarged head section 26 in which the filter material 18 is positioned. As shown, the cutting device 20 is monolithic with the head section 26 comprising plastic as well.

In the embodiment of FIGS. 3 to 6 in detail, the cutting device comprises a semi-circular projection 28 covering about 180° of the circumference of the housing 24 or head section 26 and rising from a low end 30 to a high end 32. In the top view as shown in FIG. 5, the projection 28 may have the shape of a semi-circle.

The projection 28 is rising in an angle of about 20° from the plane of the connector base or the plane of the foil or plastic closure seal, and in the exemplary embodiment of about 19.6°. The wall thickness of the projection 28, on the one hand, is decreasing from its low end 30 to its high end 32 and simultaneously is tapering from bottom to top. In this way at the high end 32 a cutting edge 34 is formed.

In a preferred embodiment corresponding to the dimensions of the air inlet 16 in connection members 4 or screw caps 5, respectively, obtainable on the market, the housing 24 has an exterior diameter of about 8 mm. The head section 26 has an exterior diameter of about 10.2 mm, the projection 28 an exterior diameter of about 9.2 mm, and an interior diameter of about 6.4 mm. The height of the housing is about 12 mm, especially 11.68 mm, and the projection 28 has a maximal height of about 5 mm, especially 4.87 mm.

As can be noted from FIG. 6, the housing 24 in the region of its bottom end is provided on the interior with annular monolithic projections 36 by means of which a positive or friction fit can be obtained with the air inlet 16.

Due to the fact that the air inlet 16 contrary to the liquid inlet 22 being centrally positioned in the connection member 4 or the screw cap 5, respectively, is eccentrically positioned and is connected to the ambient air by means of a lateral channel 17, the cutting device 20 during the screwing on or the pressing on of the connection member 4 opens the foil closure 3 sufficiently such that the gravity feed of the enteral liquid contained in the container 2 can commence.

FIGS. 7 to 11 show in more detail a second embodiment. As shown, here, too, the valve 114 is not a check valve but instead as an oleophobic filter material 118. The oleophobic filter material 118 is covering the air inlet 116 projecting into the connection member such that air can flow into the container 2 without hindrance, while the oily enteral liquid is rejected by the olephobic filter material 118.

Again, valve 114 is provided with a cutting device generally designated by 120 positioned on the side of the container 2 which during the connection of the connection member 4 with the container 2 is cutting the foil closing the container 2 when in the delivered state.

As it can be seen from FIGS. 7 and 11, the filter material 118 is positioned in a shell-shaped housing 124 which can be put over the air inlet 116, wherein further details are shown in FIGS. 8 to 10 and 12. The housing 124 preferably comprises plastic and may be connected with the filter material 118 by overmolding.

The housing 124 may be provided with an enlarged head section 126 in which the filter material 118 is positioned.

As shown the cutting device, generally designated by 120 may be monolithic with the head section 126 by overmoulding and may comprise plastic.

In the embodiment of FIGS. 8 to 12, the cutting device 120 may be a circular projection 124 which is rising in an angle of about 20° from a low side 130 to a high side 132. The circular projection 128 is provided on the largest possible radius of the head section 126.

The circular projection 128 is divided into sector-shaped wall sections or segments 138 by means of a number of incisions 133 reaching down to the head section 126.

The incisions 133 alternatively can be formed as windows, bores or the like and have the function to prevent the possible closing of the air inlet again in case that during the pressing into the foil container seal, the foil is not completely torn apart but rather forms a flap which possibly can close the inlet again. With this embodiment, even in case such a flap should position itself over the cutting device, the incisions or windows ensure a flow that facilitates operation of the enteral liquid delivery system. Additionally a complete emptying of the small volume in the bottle neck of the container 2 is ensured.

The free top edges of the segments 138 may be provided with cutting edges 140 to facilitate cutting of the foil closure. Further, on the edges opposite either side of the incisions 133, cutting edges 142 may be provided to further facilitate the cutting of the foil closure.

Further, the incisions 133 may narrow in the direction of the head section 126 and may slightly taper, for example in an angle of 2°, to improve the cutting performance and to facilitate the ejection of the from the plastic injection moulding apparatus from which they are created.

In a preferred embodiment according to the dimensions of the air inlet 116 in connection members 4 or screw caps 5, respectively, available on the market, the housing 124 has an exterior diameter of about 8 mm. The head section 126 has an exterior diameter of about 10 mm, the circular projection 128 an exterior diameter of about 9 mm and an interior diameter of about 7 mm. The height of the housing 124 is about 16 mm, especially 16.55 mm, on the high side 132, at about 13 mm on the low side 130. Correspondingly the projection 128 has a maximal height of about 5 mm and a minimal height of about 1.8 mm.

As can be noted from FIG. 11, the housing 124 in the area of its bottom end has a slight conical surface on its interior to provide for a friction fit with the air inlet 116.

Since, as can be noted from FIG. 7, the air inlet contrary to the centrally positioned fluid outlet 122 in the connection member 4 or the screw head 5, respectively, is eccentrically positioned and is connected by a lateral channel 117 with the ambient air, the cutting device 120 during the screwing on or pressing on of the connection member 4 sufficiently cuts the foil closure 3 such that the gravity feed of the enteral liquid contained in the container 2 can start via liquid channel 122.

For the sake of completeness it is to be noted that filter material 18, 118 is not shown in FIGS. 3 to 5 and 7 for the sake of a clearer description of certain aspects and features.

In FIGS. 13 to 16 additionally in a side view and cross-section further embodiments of the apparatus 1 are shown which are showing the connection of the housing 24 with the filter material 18 and the cutting device 20 by overmoulding, wherein the representation in these Figures is self-explanatory with no further description being necessary.

The disclosed embodiments are of simple construction, yet provide a reliable air valve for operating pressures to which it is suited. It is believed that with the construction of these valves as disclosed, the air flow and thus enteral fluid flow can be accurately predetermined and regulated. In this manner, the present invention avoids complicated designs and yet may result in reliably achieving the above-noted air valve functionality. Further, the design of the above-described embodiments avoids complicated assembly methods by way of limiting the number of highly toleranced dimensions or assembly methods and the like and thus they may lend themselves to assemblage by automated equipment.

It should be appreciated that the apparatus of the present invention is capable of being incorporated in the form of a variety of embodiments, only some of which have been illustrated and described above. The invention may be embodied in other forms without departing from its spirit or essential characteristics. The described embodiments are to be considered in all respects only as illustrative and not restrictive, and the scope of the invention is, therefore, indicated by the appended claims rather than by the foregoing description. All changes which come within the meaning and range of equivalency of the claims are to be embraced within their scope.

What is claimed is:

1. Apparatus for introducing air into an enteral container having a planar foil closure of aluminum or plastic closing the container when initially delivered, having a valve positioned in a connection member connecting the enteral instrument with the container containing the enteral liquid and which is controlling the introduction of air via an air inlet that corresponds to the consumption of the enteral liquid, wherein the valve includes a filter material covering the air inlet in the connection member, and wherein the connection member on the side lying in the direction of the container includes a cutting device for the foil closure of aluminum or plastic initially closing the container, wherein the improvement comprises the filter material comprises an oleophobic filter material positioned in a shell-shaped housing (24, 124) mounted over the air inlet (16, 116) facing the container (2). and the cutting device (20, 120) positioned on the shell-shaped housing (24, 124) on the side of the valve (14, 114) facing the container (2) wherein the cutting device (20, 120) comprises a circular or partly circular projection (28, 128) rising from a low side (3O, 130) to a high side (32, 132).

2. The apparatus of claim 1, wherein the improvement further includes a head section (26) on the cutting device and the circular or partly circular projection is separated into segments (36) by windows or incisions (33) extending to the head section (26).

3. The apparatus of claim 2, wherein the improvement further comprises the housing (24) comprising plastic overmolded over the filter material (18).

4. The apparatus of claim 3, wherein the improvement further comprises a broadened head section (26) of the housing (24), and the filter material (18) positioned in the broadened head section (26) of the housing (24).

5. The apparatus of claim 4, wherein the improvement further comprises the rise of the circular projection (24) from the low side (30) to the high side (32) is about 20° from the planar foil closure.

6. The apparatus of claim 5, wherein the improvement further comprises one or more of the circular or partly circular projections (28, 128) or segments (138) provided with an upper cutting edge (40,140).

7. The apparatus of claim 6, wherein the improvement further comprises one or more of the edges of the incisions (33) provided with a cutting edge (42).

8. The apparatus of claim 7, wherein the improvement further comprises one or more of the incisions (33) narrow as they approach the head section (26).

9. The apparatus of claim 8, wherein the improvement further comprises the wall thickness of the projection (28) from its low end (30) to its high end (32) decreases such that at the high end (32), a cutting edge (34) is formed.

10. The apparatus as in any of claims 2-9, wherein the improvement further comprises the housing (24) having an interior adapted to slidingly and frictionally engage the air inlet (16).

11. The apparatus as in any of claims 2-9, wherein the improvement further comprises the interior of the housing (24) having one or more annular unitary projections (36) to provide for a positive or friction fit with the air inlet (16).

12. The apparatus of claim 4, wherein the improvement further comprises one or more of the edges of the incisions (33) provided with a cutting edge (42).

13. The apparatus of claim 4, wherein the improvement further comprises one or more of the incisions (33) narrow as they approach the head section (26).

14. The apparatus of claim 2, wherein the improvement further comprises one or more of the edges of the incisions (33) provided with a cutting edge (42).

15. The apparatus of claim 14, wherein the improvement further comprises one or more of the circular or partly circular projections (28, 128) or segments (138) provided with an upper cutting edge (40,140).

16. The apparatus of claim 2, wherein the improvement further comprises one or more of the circular or partly circular projections (28, 128) or segments (138) provided with an upper cutting edge (40,140).

17. The apparatus of claim 16, wherein the improvement further comprises one or more of the edges of the incisions (33) provided with a cutting edge (42).

18. The apparatus of claim 16, wherein the improvement further comprises one or more of the incisions (33) narrow as they approach the head section (26).

19. The apparatus of claim 1, wherein the improvement further comprises the circular or partly circular projection (28, 128) provided with an upper cutting elge (40, 140).

20. The apparatus of claim 19, wherein the improvement further comprises the housing (24) comprising plastic overmolded over the filter material (18) and the housing including a broadened head section (26).

21. The apparatus of claim 20, wherein the improvement further comprises the wall thickness of the projection (28) from its low end (30) to its high end (32) decreases such that at the high end (32), a cutting edge 34 is formed.

22. The apparatus of claim 21, wherein the improvement further comprises the housing (24) having an interior adapted to slidingly and frictionally engage the air inlet (16).

23. The apparatus of claim 21, wherein the improvement further comprises the interior of the housing (24) having one or more annular unitary projections (36) to provide for a positive or friction fit with the air inlet (16).

24. The apparatus of claim 19, wherein the improvement further comprises a head section (26) on the cutting device and the circular or partly circular projection is separated into segments (36) by windows or incisions (33) extending to the head section (26) and one or more of the circular or partly circular the segments (138 provided with an upper cutting edge (40,140).

25. The apparatus of claim 24, wherein the improvement further comprises the housing (24) having an interior adapted to slidingly and frictionally engage the air inlet (16).

26. The apparatus of claim 24, wherein the improvement further comprises the interior of the housing (24) having one or more annular unitary projections (36) to provide for a positive or friction fit with the air inlet (16).

27. The apparatus of claim 19, wherein the improvement further comprises the housing (24) having an interior adapted to slidingly and frictionally engage the air inlet (16).

28. The apparatus of claim 19, wherein the improvement further comprises the interior of the housing (24) having one or more annular unitary projections (36) to provide for a positive or friction fit with the air inlet (16).

29. The apparatus of claim 1, wherein the improvement further comprises a housing (24) with the filter material (18) positioned in the housing, and the housing (24) comprising plastic overmolded over the filter material (18).

30. The apparatus of claim 29, wherein the improvement further comprises one or more of the circular or partly circular projections (28, 128) provided with an upper cutting edge (40,140).

31. The apparatus of claim 30, wherein the improvement further comprises a head section (26) on the cutting device and the circular or partly circular projection is separated into segments (36) by windows or incisions (33) extending to the head section (26).

32. The apparatus of claim 31, wherein the improvement further comprises the housing (24) having an interior adapted to slidingly and frictionally engage the air inlet (16).

33. The apparatus of claim 31, wherein the improvement further comprises the interior of the housing (24) having one or more annular unitary projections (36) to provide for a positive or friction fit with the air inlet (16).

34. The apparatus of claim 29, wherein the improvement further comprises the housing (24) having an interior adapted to slidingly and frictionally engage the air inlet (16).

35. The apparatus of claim 29, wherein the improvement further comprises the interior of the housing (24) having one or more annular unitary projections (36) to provide for a positive or friction fit with the air inlet (16).

36. The apparatus of claim 29 wherein the improvement further comprises a head section (26) on the cutting device and the circular or partly circular projection is separated into segments (36) by windows or incisions (33) extending to the head section (26) with one or more incisions (33) narrowing as they approach the head section (26).

37. The apparatus of claim 36, wherein the improvement further comprises one or more edges of the incisions (33) provided with a cutting edge (42).

38. The apparatus of claim 37, wherein the improvement further comprises the housing (24) having an interior adapted to slidingly and frictionally engage the air inlet (16).

39. The apparatus of claim 37, wherein the improvement further comprises the interior of the housing (24) having one or more annular unitary projections (36) to provide for a positive or friction fit with the air inlet (16).

40. The apparatus of claim 36, wherein the improvement further comprises the wall thickness of at least one of the segments (36) from its low end (30) to its high end (32) decreases such that at the high end (32), a cuffing edge (34) is formed.

41. The apparatus of claim 40, wherein the improvement further comprises one or more of the edges of the incisions (33) provided with a cuffing edge (42).

42. The apparatus of claim 41, wherein the improvement further comprises the housing (24) having an interior adapted to slidingly and frictionally engage the air inlet (16).

43. The apparatus of claim 41, wherein the improvement further comprises the interior of the housing (24) having one or more annular unitary projections (36) to provide for a positive or friction fit with the air inlet (16).

44. The apparatus of claim 1, wherein the improvement further comprises the wall thickness of the projection (28) from its low end (30) to its high end (32) decreases such that at the high end (32), a cutting edge 34 is formed.

45. The apparatus of claim 44, wherein the improvement further comprises the housing (24) having an interior adapted to slidingly and frictionally engage the air inlet (16).

46. The apparatus of claim 44, wherein the improvement further comprises the interior of the housing (24) having one or more annular unitary projections (36) to provide for a positive or friction fit with the air inlet (16).

47. The apparatus of claim 44, wherein the improvement further comprises a head section (26) on the cutting device and the circular or partly circular projection is separated into segments (36) by windows or incisions (33) extending to the head section (26) with one or more incisions (33) narrowing as they approach the head section (26).

48. The apparatus of claim 47, wherein the improvement further comprises the housing having an interior adapted to slidingly and frictionally engage the air inlet (16).

49. The apparatus of claim 47, wherein the improvement further comprises the housing (24) having one or more annular unitary projections (36) to provide for a positive or friction fit with the air inlet (16).

* * * * *

UNITED STATES PATENT AND TRADEMARK OFFICE
CERTIFICATE OF CORRECTION

| | |
|---|---|
| PATENT NO. | : 7,516,765 B2 |
| APPLICATION NO. | : 11/284636 |
| DATED | : April 14, 2009 |
| INVENTOR(S) | : Brendan Hogan et al. |

Page 1 of 1

It is certified that error appears in the above-identified patent and that said Letters Patent is hereby corrected as shown below:

On the Title Page

Item (75), delete "Gort" and substitute --Coole Demense-- in its place.

In the Claims

In column 6, claim 1, line 32, immediately after "the container (2)" delete "." and substitute --,-- in its place.

In column 7, claim 24, line 55, after "the segments (138" insert --)--.

In column 8, claim 40, line 51, before "edge (34) is" delete "cuffing" and substitute --cutting-- in its place.

In column 8, claim 41, line 55, after "provided with a" delete "cuffing" and substitute --cutting-- in its place.

In column 8, claim 44, line 66, after "a cutting edge" delete "34" and substitute --(34)-- in its place.

Signed and Sealed this

Twenty-fifth Day of August, 2009

David J. Kappos
*Director of the United States Patent and Trademark Office*